United States Patent
Bowers

(10) Patent No.: US 7,703,148 B2
(45) Date of Patent: Apr. 27, 2010

(54) LIGHT OCCLUSIVE EYELID COVER THAT PERMITS UNINHIBITED SIGHT

(76) Inventor: Adrian Hardwick Bowers, 1555 Roma Ct., Reno, NV (US) 89523

( * ) Notice: Subject to any disclaimer, the term of this patent is extended or adjusted under 35 U.S.C. 154(b) by 1055 days.

(21) Appl. No.: 11/163,673

(22) Filed: Oct. 26, 2005

(65) Prior Publication Data

US 2007/0089217 A1  Apr. 26, 2007

(51) Int. Cl.
*A61F 9/02* (2006.01)
(52) U.S. Cl. .................................................. 2/12
(58) Field of Classification Search ........... 2/12, 2/15; 128/858
See application file for complete search history.

(56) References Cited

U.S. PATENT DOCUMENTS

| | | | |
|---|---|---|---|
| 1,924,315 A | | 8/1933 | Hemphill |
| 2,671,898 A | | 3/1954 | Wade |
| 2,891,252 A | | 6/1959 | Lazo |
| 2,942,270 A | * | 6/1960 | Enright .............. 2/15 |
| 3,068,863 A | | 12/1962 | Bowman |
| 3,300,786 A | * | 1/1967 | Rosenvold et. al. ........ 2/15 |
| 3,619,815 A | * | 11/1971 | Towner .............. 2/12 |
| 3,780,379 A | | 12/1973 | Kampman |
| 4,599,746 A | | 7/1986 | Stoner |
| 4,682,371 A | | 7/1987 | Heltman |
| 4,790,031 A | | 12/1988 | Duerer |
| 4,872,217 A | | 10/1989 | Kitayama |
| 4,944,040 A | | 7/1990 | Riedel et al. |
| 4,951,658 A | | 8/1990 | Morgan et al. |
| 4,979,811 A | | 12/1990 | Boyer |
| 5,191,897 A | * | 3/1993 | Meshel .............. 600/558 |
| 5,435,006 A | | 7/1995 | Kitayama |
| 5,741,582 A | | 4/1998 | Leaderman et al. |
| 5,940,886 A | | 8/1999 | McCarthy |
| 6,320,094 B1 | * | 11/2001 | Arnold et al. ........ 602/54 |
| 6,543,056 B2 | | 4/2003 | Spiteri |
| 6,571,799 B1 | | 6/2003 | Daly |
| 6,745,397 B2 | | 6/2004 | Magidson |
| 2004/0074502 A1 | * | 4/2004 | Abbasi .............. 128/858 |

* cited by examiner

*Primary Examiner*—Katherine Moran
(74) *Attorney, Agent, or Firm*—Aventerprise, LLC.

(57) ABSTRACT

An improved sleeping eyelid cover that blocks a significant portion of light from entering a closed eye by way of the eyelid and allows uninhibited sight. The eyelid cover is safe and comfortable and conceived to be used as a sleep aid. The front side (14) and back side (16) of the eyelid cover are made of a flexible material that enables the eyelid cover to fold into (or out from) the ocular cavity and allow uninhibited sight for the wearer by the wearer opening his/her eyes. The eyelid cover attaches to the eye be way of adhesive which may be applied to the back side (16) of the cover in any number of configurations including small adhesive dots (18). Further, the eyelid cover may be composed of numerous layers of material to aid in blocking light.

10 Claims, 4 Drawing Sheets

LIGHT OCCLUSIVE EYELID COVER THAT PERMITS UNINHIBITED SIGHT

BACKGROUND OF THE INVENTION

1. Field of Invention

This invention generally relates to eyelid covers, specifically to such eyelid covers that help block light from entering the eye by way of the eyelid to aid in sleep.

2. Prior Art

Light entering the eye through the eyelid can either be a nuisance or can even cause damage to the retina (for example when sunbathing). Light that enters the eye through a closed eyelid while sleeping can disrupt sleep patterns (for example when someone wants to sleep until after the sun has risen, but is bothered by ambient light entering through opaque curtains in the bedroom, which causes the individual to inadvertently awaken). Previously, various means of light occluding methods have been used to block unwanted light from entering the eye through the eyelid. Methods have included sleep masks that cover both eyes and have some sort of retention device, eyelid covers that are self-adherent or have a retention device, and light occluding curtain backings. These light occluding methods have served a number of end functions including medical eye exams, therapy for specific eye disorders, sunbathing, and sleep aids. However, all of these previous methods tend to have drawbacks including that they are 1) uncomfortable to wear, 2) are not easy to wear, 3) impede normal vision when in use, and 4) specifically related to sleep aids, disrupt sleep by unintended effects of their use.

Related to sleep aids, various forms of light occluding inventions have been made. For example, U.S. Pat. No. 5,741,582 to Leaderman and Fradin (1998) invented light occluding curtains that can be used in conjunction with normal draperies to help block out unwanted light to aid in sleep. These curtains are expensive to manufacture, are heavy, and significantly distort the normal look of draperies (for example, all light is blocked causing an overly dark look to a room during the day when a more diffuse light coming through a curtain may be desirable). Another problem with light occlusive curtains is that they must be used in every room where one wants to sleep, this may be inhibitive when sleeping in multiple rooms or traveling.

One inadequate solution to the above problems relates to light occlusive devices that are worn on the body, either as a sleep mask or as an eyelid cover. These devices solve the problem of traveling to other areas where light blocking curtains are not installed; but unfortunately, these worn devices cause other problems such as discomfort, interruption of normal sleep patterns, and interference with normal vision. U.S. Pat. No. 6,543,056 to Spiteri (2003) describes a modified sleep mask that purports to be an improvement on traditional sleep masks. Also, U.S. Pat. No. 4,872,217 to Kitayama (1989) describes an invention that is worn as a sleep mask to block light from entering the eye through the eyelid. Although this invention purports to be an improvement due to its ability to not contact the eyelid, this invention shares the same drawbacks of all sleep masks. Namely, the drawbacks of sleep masks include: 1) interference with normal sight (for example, the sleep mask must be manually removed to see clearly) and 2) the sleep mask contacts some part of the face or head of the wearer. These contact points are likely to become sleep disruptive pressure points, when the weight of the wearer's head sandwiches the sleep mask between the pillow and the wearer's face or eyes. Further, since sleep masks interfere with sight, they can create a claustrophobic feeling for the wearer, which is exacerbated by a potential need to remove the sleep mask rapidly while the wearer is in a somnolent state.

A continual problem for light occlusive sleep masks and eyelid covers is this need to remove the invention before one can obtain normal sight. For some inventions this is not a huge problem since their usage is in light occlusive therapy (in light occlusive therapy there is a strict amount of time that the devices are worn where during the wear-time the function is to block all or most light from entering the eye). For example see U.S. Pat. No. 4,944,040 to Riedel and Olsen (1990); U.S. Pat. No. 5,191,897 to Meshel (1993); and U.S. Pat. No. 4,951,658 to Morgan and Wyszynski (1989). However, most eyelid covers that have been invented that block light from entering the eye through the eyelid suffer from this problem of need for removal or manipulation in order for the wearer to see normally. For example see U.S. Pat. No. 5,191,897 to Meshel (1993) and U.S. Pat. No. 4,599,746 to Stoner (1986). The one known exception to this problem relates to an expired U.S. patent to Towner (1971) (U.S. Pat. No. 3,619,815).

Towner (1971), U.S. Pat. No. 3,619,815, represents the closest known prior art; however, substantial differences in use and function exist when compared to the present invention. Towner (1971) invented an "eyelid shield" that was "substantially opaque" to protect the eyes while "sunbathing" or for use by "outdoor workmen and others exposed to bright sunlight or overhead lighting". Further, Towner's device was "domed" being "semi-ovate" and constructed of "thin plastic sheet material" that was attached to the eyelid by adhesive. Towner's device also had an integral "eyeshade" which was a "unilateral forwardly extending translucent portion shading the eyes when open" (page 1-2, U.S. Pat. No. 3,619,815). Towner (1971) makes no mention of use of this device for a sleep aid. Further, the device that Towner claims would be wholly inadequate as a sleep aid.

Worn sleep aids such as sleep masks and eyelid covers, as previously mentioned, must be extremely comfortable so as to not interfere with sleep. Towner's (1971) device is made of plastic, is in a semispherical construction, and includes an extended eyeshade. These three features preclude the use of this device for a sleep aid and his device is of questionable utility in general. Towner states that his device is made of plastic but able to fold into the ocular cavity atop of the eyelid. Plastic, even when thin, is not the most flexible material. It seems unlikely that the device could easily fold into the ocular cavity atop of the eyelid as Towner describes. Even if the device could fold as described, it would necessitate the use of a much stronger adhesive than if the device had been made of a superior, more flexible, material that would fold atop the eyelid in an easier manner. Further, once folded in the ocular cavity plastic is likely to return to its formed shape more readily than superior materials. This force to return to its formed original shape would create undue pressure on the top of the eyeball and ocular cavity tissue. (Please see FIG. 5 of Towner (1971)). Also, Towner's device is made of plastic which is unsuitable for a sleep aid. Plastic will prevent the eyelid skin from the contact with the air which will in turn cause heat and moisture buildup under the device. These unpleasant sensations are not conducive to sleep.

Towner's (1971) "domed" and "semi-ovate" semispherical construction is problematic for a sleep aid. When sleeping, various forces are placed on the face and eyelid by way of pressure of gravity from the head and face resting on the pillow (if someone is sleeping on their stomach or on their side). As such, these forces tend to distort the shape of the eyelid atop the eyeball into some other shape other than the usual semispherical shape. Towner's device would likely be very uncomfortable in these situations. Additionally, since Towner's invention is "domed" and "semi-ovate", if part of it were to become depressed (such as from force exerted by the pillow) when the force was removed it would snap back to its original shape. This return to original shape would likely be accompanied by both a sound made by the plastic and a sensation of the skin of the eyelid being pulled. Both the sound and the pulling-skin-sensation would not be comfortable nor conducive to sleep. A further problem with a preformed "domed" "semi-ovate" shape is that everyone's eyeballs and eyelids are of a different size and shape. For example, if someone had larger or smaller eyelids the preformed size of Towner's device would not fit those individuals.

Towner's (1971) device has an extended eyeshade that protrudes from the front of the device. This eyeshade would contact the pillow while sleeping and either pull the eyelid cover off or exert pressure on the tissue around the eye. Again, Towner's device was not conceived for use as a sleep aid and would be unsuitable as such.

The fundamental safety of Towner's (1971) device, as conceived, or as used as a sleep aid is questionable. Towner describes the device as made of "thin plastic sheet material" (page 2; U.S. Pat. No. 3,619,815). Thin plastic has a thin, yet sharp, edge. For example, thin plastic is about the same thickness of thin paper. Paper can easily cut skin. Furthermore, the proximity of something that could cut skin being close to the eye is dangerous. Additionally, the eyeshade extension that Towner (1971) describes, or another part of the device, could bend back and cut the eyeball if force where exerted on it by a pillow while sleeping. Again, any edge of the device could cut the eye while someone was applying the device. A cut to the eyeball, face, or eyelid is highly dangerous and highly undesirable.

In summary, all prior inventions designed to help block light from the eye by way of entry through the eyelid suffer from some or all of the following disadvantages:

(a) They are expensive to manufacture. This cost prohibits the sale of these products to a wide variety of consumers.

(b) They are heavy. For example, light-blocking drapery liners can strain or damage curtain rod assemblies.

(c) Do to their size they are unable to be used while traveling. For example, the use of light-blocking drapery liners is prohibitive while traveling due to the unknown constraints of fitting the window in which the traveler finds himself/herself.

(d) They interfere with the sleep process due to their uncomfortable nature. For example, sleep masks invariably create a sensation of something that is covering the eyes or face. This can either be prohibitive due to pressure that is exerted on the eyes, face, or head of the wearer or through a psychological process of causing claustrophobia.

(e) They interfere with the sleep process because their usage is incompatible with the physiological necessities of sleep. For example, if one chooses to put on or take off eyelid covers or a sleep mask, these processes of putting on or taking off the device, would necessitate a certain amount of physiological arousal. In turn, this physiological arousal is likely to result in the person entering a more awake state from a formerly somnolent state—which is incompatible with sleep. Further, prior art sleep masks and eyelid covers present a problem in that one must be somewhat awake to put them on correctly. This is problematic if one wants to read before going to sleep and fall asleep without fiddling with the application of a sleep mask or eyelid cover. The actual application of a sleep mask or eyelid cover, after some preferred pre-sleep behavior such as reading, is likely to cause physiological arousal thereby being incompatible with sleep.

(f) They interfere with normal vision. Currently, all known prior inventions that are designed to be sleep aids when worn on the eyelid, face, or head interfere with normal vision. Towner (1971) is the lone exception, but his device was not conceived as a sleep aid. And, more importantly, for the previously discussed reasons, Towner's (1971) device is generally dangerous and wholly unsuitable as a sleep aid. The interference with normal vision and the special demands of sleeping are substantial. For example, sleep masks or various eyelid covers must be removed in order to see out of the eyes. The interference of normal vision is problematic because often the user would like to see instantly without engaging the process of removing the inventions from the eyelid, face, or head. For example, someone that is asleep may be awakened by a home intruder and instantly want use of their sight. Similarly, a soldier who is sleeping in a combat condition during the day, in extreme dessert sun, may want the benefits of a light-occluding device, but would not use the prior art due to the drawback of the inability to instantly have use of his/her sight. Further, all known prior art related to sleep aids prohibits normal vision. Therefore, one cannot read before going to sleep with prior art inventions and cannot instantly open his/her eyes to see something in the bedroom such as an alarm clock.

(g) They are of varying ability to actually block light from entering the eye through the eyelid. For example some sleep masks when worn do not fit the contours of the face and allow light to enter these spaces between the face and the mask.

(h) They are of non-adjustable ability to block light from entering the eye through the eyelid. For example, often an eyelid cover blocks all light or for U.S. Pat. No. 4,944,040 to Riedel and Olsen (1990) the eyelid cover blocks certain wavelengths of light. However, no known prior art blocks varying amounts of light. For example, no known prior art sleep masks or eyelid covers are designed to block 50 percent of light or 75 percent of light or 95 percent of light. Sometimes a consumer may want to wear an eyelid cover that blocks only 50 percent of light so awakening in the morning is more easy due to more light entering the eye through the eyelid. Conversely, another consumer may want to wear an eyelid cover that blocks 95 percent of light or higher so that he/she can sleep effectively in an intense light environment.

(i) They are dangerous and not conceived as a sleep aid. In particular, Towner's (1971) device is, as previously discussed, 1) generally dangerous, 2) not conceived as a sleep aid, and 3) incapable of being a sleep aid due to safety and comfort factors.

OBJECTS AND ADVANTAGES

Accordingly, several objects and advantages will become apparent from a consideration of the ensuing description and drawings. These objects and advantages include the following:

(a) to provide an eyelid cover that is inexpensive to manufacture thereby increasing the likelihood that a wide variety of consumers will be able to purchase the invention;

(b) to provide an eyelid cover that is light in weight;

(c) to provide an eyelid cover that is easily portable to be used at home or while traveling, camping, or in any place where a portable light-blocking eyelid cover would be beneficial.

(d) to provide an eyelid cover that does not interfere with the sleep process. For example, an eyelid cover that is comfortable, and does not create undue pressure on the face, eyes, or head; to provide an eyelid cover that is barely detectable to the wearer and does not contribute to feelings of claustrophobia.

(e) to provide an eyelid cover that does not interfere with the physiological necessities of sleep. For example, to provide an eyelid cover that one can put on before going to sleep and that does not need to be adjusted to obtain normal vision. Therefore, one can read before going to sleep with the eyelid cover on his/her eyelids, go to sleep without adjusting the eyelid covers, and open his/her eyes to see things with normal vision throughout the night and day. All of this can be accomplished without adjusting the eyelid covers and therefore, without increasing physiological arousal which could interfere with sleep. Further, the invention is less likely to cause the claustrophobic reaction that sleep masks and prior art eyelid covers can evoke in some individuals.

(f) to provide an eyelid cover that does not interfere with normal vision. The invention can be worn with the eyelids open or with the eyelids closed and the invention does not inhibit normal vision when the eyelids are open. The ability of the invention to accomplish this advantage is particularly useful for individuals that would like instant use of their sight. Some examples of these individuals could be vigilant sleepers that are concerned about visually checking the clock, checking unknown sounds in the room, or checking any potential safety threats while sleeping, such as possible house fires or intruders. Other individuals that could want instant use of their site include travelers in potentially unsafe settings or military soldiers in combat conditions that necessitate the instant assessment of threat and/or use of weaponry or machinery.

(g) to provide an eyelid cover that blocks a significant percentage of light from entering a closed eye by way of the eyelid.

(h) to provide an eyelid cover that is capable of being manufactured to block varying percentages of light from entering an eye by way of the eyelid. Various differences in manufacturing could produce eyelid covers of different abilities to block different amounts of light. This could be advantageous in that one individual may want an eyelid cover that blocks some but not all light (50 percent for example). The individual may want this 50 percent blocking eyelid cover to effectively block diffuse sunlight coming through a curtain, but may still want to experience some light coming through the eyelid to aid in waking up. However, another individual may want an eyelid cover of a higher light-blocking percentage (for example 95 percent). A situation where this may be useful is when trying to sleep in intense light environments, for example a soldier who must sleep in the desert sun or an individual that wants to block out as much ambient light as possible while sleeping late into the morning in their bedroom.

(i) to provide a safe and comfortable sleep aid that blocks light from entering the eye by way of the eyelid, but does not interfere with normal vision.

Further objects and advantages are to provide a light-blocking eyelid cover that does not interfere with normal vision. Additionally, the eyelid cover could be used multiple times or as a disposable item depending on manufacturing. Still further objects and advantages will become apparent from a consideration of the ensuing description and drawings.

SUMMARY

In accordance with the present invention, the eyelid cover when the eye is closed blocks a significant amount of light from entering the eye by way of the eyelid. Further, the eyelid cover can be worn with the eye open (e.g. it retracts into the ocular cavity atop of the eyelid). Therefore, the eyelid cover does not interfere with normal vision. This advantage is a substantial improvement over all known prior art sleep aids.

In the drawings, closely related figures have the same number but different alphabetic suffixes.

DRAWINGS—FIGURES

FIGS. 1A to 1D show various aspects of an eyelid cover that is of a flat design with adhesive dots on one side only.

FIG. 2A shows a front view of the eyelid cover (of FIGS. 1A to 1D) in use on a human's eyelid with an open eye. Likewise, FIG. 2B shows a front view of the eyelid cover (of FIGS. 1A to 1D) in use on a human's eyelid with a closed eye. And FIG. 2C shows a side view of the eyelid cover (of FIGS. 1A to 1D) in use on a human's eyelid with an open eye.

Figure 1A:
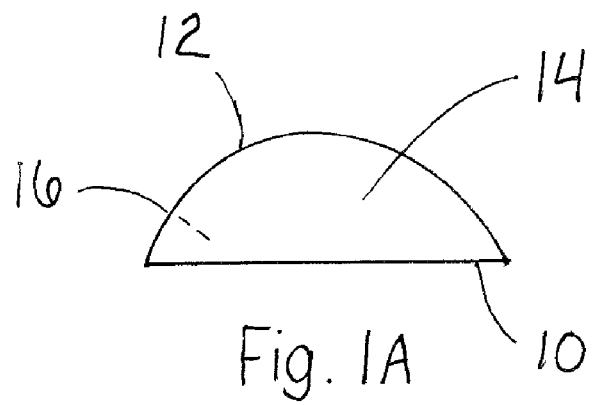

| DRAWINGS - REFERENCE NUMERALS | |
| --- | --- |
| 10 | anterior edge |
| 12 | posterior edge |
| 14 | front of cover |
| 16 | back side of cover |
| 18 | adhesive dots |
| 20 | side view of preferred embodiment |
| 22 | side view of alt. embodiment |
| 24 | side view of material one |
| 26 | side view of material two |
| 28 | concentric marking lines |

DETAILED DESCRIPTION—PREFERRED EMBODIMENT—FIGS.

Figure 1B:
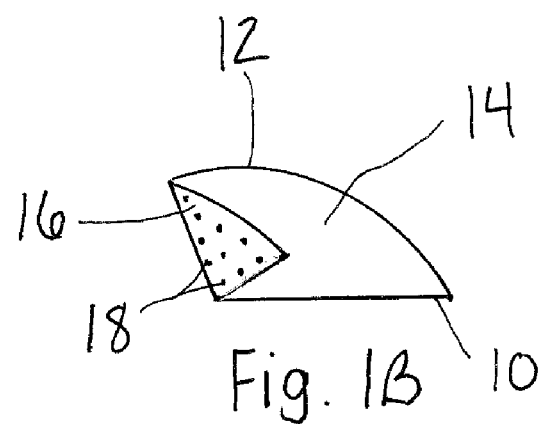
Figure 1C:
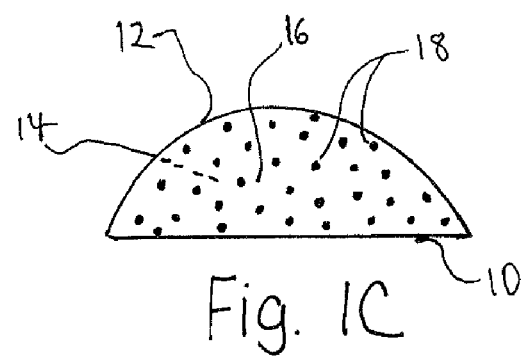
Figure 1D:
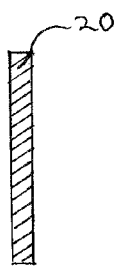

A preferred embodiment of the eyelid cover of the present invention is illustrated in FIG. 1A (front view), FIG. 1B eyelid cover bent to show front and back, FIG. 1C (back view), and FIG. 1D (side view enlarged). The eyelid cover is comprised of a thin uniform sheet member material that is cut in the approximate shape to cover an adult human's upper eyelid from where the skin of the eyelid meets the eyelashes to right below the eyebrow. In the preferred embodiment the sheet member is of a natural black-dyed silk fabric of tight weave and high thread count to maximize both comfort of the soft silk fabric, its ability to moderate heat and humidity on the skin, and its ability to block light. However, other fabrics or sheet materials would also make acceptable substitutes. These could include: nylon, rayon, Kevlar, cotton, and various other thin, flexible, light-blocking materials, including polymeric materials. The back side of the eyelid cover is covered in a hypoallergenic adhesive. The preferred embodiment uses adhesive dots 18 spaced on the back side 16 so the fabric material and skin can adequately breathe when affixed to the eyelid.

At one end of the eyelid cover is a straight (or only very slightly curved) edge 10. This edge is designed to correspond to the skin of the upper eyelid where it meets the eyelashes. The other edge of the eyelid cover is more curved 12 and designed to match the curve where the upper eyelid meets the eyebrow.

The rough shape of the eyelid cover is a flat semi-oval. This shape can be cut from a larger sheet of material by programmed robotic cutters including laser cutters or by hand. The length is typically 50 mm. The width at the widest part of the semi-oval is typically 25 mm. The thickness of the material that comprises the eyelid cover is quite thin and in general less than 0.3 mm. The outer edges of the eyelid cover 10 & 12 may be micro-abraded or sealed in some fashion to increase the softness of the edges and decrease the likelihood of the edges fraying.

The adhesive on the back side of the preferred embodiment eyelid cover is applied in dots 18 roughly equally spaced over the entire back side 16. However, other embodiments can have adhesive dots 18 placed on the back of the cover 16 in other configurations. Further, other embodiments may have a more uniform and continual adhesive applied to the entire backside 16 of the cover. Adhesive can be applied by any number of means including by spray devices, by pressure transfer adhesives, by brush, etceteras.

Operation—Preferred Embodiment—FIGS. 1, & 2

The manner of using the eyelid cover is to affix it to the skin of the upper eyelid from where the eyelid meets the eyelashes to the skin all the way to right below the eyebrow. One first positions the anterior edge 10 to be parallel to the edge of the upper eyelid where the eyelashes begin. Then, the front 14 of the eyelid cover is depressed by the fingers causing the backside 16 to come into contact with and adhere to the skin of the eyelid. This process is simplified by putting one eyelid cover on at a time. Further ease is accomplished by pulling the skin of the upper eyelid as taut as possible before and during application. This can be done by almost closing the eye and furrowing the forehead skin, thus raising the eyebrows by way of the muscles in the forehead.

Figure 2A:
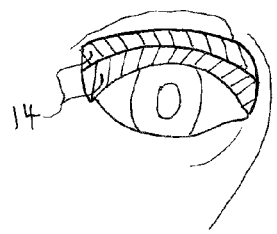
Figure 2B:
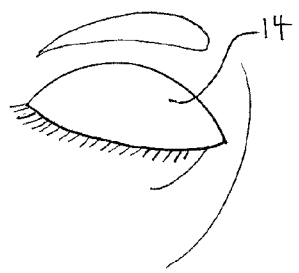
Figure 2C:
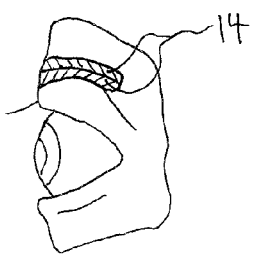

When the eyelid is closed (FIG. 2B), the eyelid cover adheres to the skin of the upper eyelid and blocks a significant portion of light that would otherwise enter the eye by passing through the eyelid. However, as seen in FIGS. 2A and 2C when the eye is opened the eyelid cover folds into the ocular cavity above the eye allowing the individual to see normally.

To remove the eyelid cover, one simply slowly pulls one edge 12 of the cover away from the skin of the eyelid and gradually peels the eyelid cover off. Since the preferred material is so supple, use of a low-tack adhesive is made possible and further aids in quick and painless removal.

Depending on the composition of the adhesive (and individual differences in sebaceous gland productivity in the periorbital facial area), the eyelid cover can be either a disposable one-time-use item or can be used multiple times.

Figure 4A:
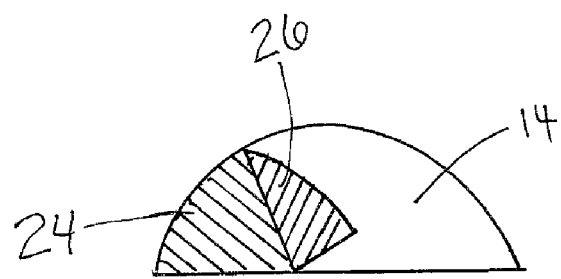
FIGS. 4A and 4B show various aspects of eyelid covers that are composed of different layers of materials.
Figure 4B:
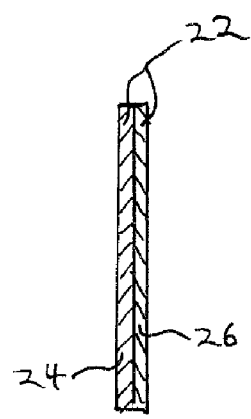
Figure 5:
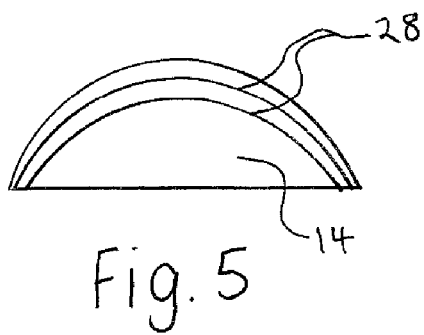
FIG. 5 shows a similar eyelid cover to the preferred embodiment with concentric marking lines to enable it to be cut-to-size by a consumer.

Description—Alternate Embodiment—FIGS. 3, 4, & 5

Figure 3A:
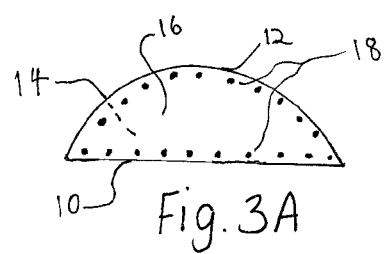
FIG. 3A shows a similar eyelid cover with adhesive dots arranged along the anterior and posterior edge on one side only of the eyelid cover.
Figure 3B:
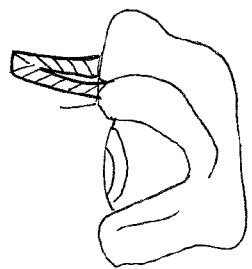
FIG. 3B shows the eyelid cover (of 3A) as a side cutaway in use on a human's open eyelid.
Figure 3C:
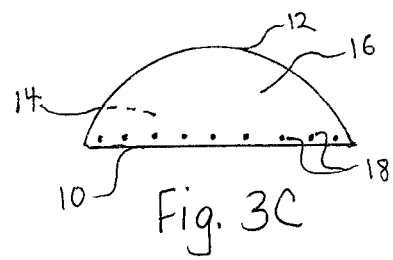
FIG. 3C shows a similar eyelid cover with adhesive dots arranged along the posterior edge on one side only of the eyelid cover.
Figure 3D:
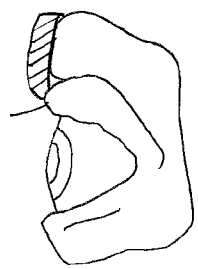
FIG. 3D shows the eyelid cover (of 3C) as a side cutaway in use on a human's open eyelid.

Additional embodiments are shown in FIGS. 3, 4, and 5. In FIG. 3A an alternate arrangement of adhesive dots 18 is provided where adhesive is placed on the back side 16; but only near the anterior 10 and posterior 12 edges. FIG. 4 depicts an alternate embodiment that is comprised of two separate sheets of material that are attached together. FIG. 4A shows this embodiment with one part of the top sheet 26 peeled back to reveal the bottom sheet 24. FIG. 4B shows an enlarged side view 22 of this embodiment with both sheets 24 & 26 attached together. FIG. 5 depicts an alternate embodiment where concentric lines 28 are drawn or printed on the top side 14 to indicate where a consumer should cut the device.

Operation—Alternate Embodiment—FIGS.

In FIG. 3A an alternate arrangement of adhesive dots 18 is provided where adhesive is placed on the back side 16, but only near the anterior 10 and posterior 12 edges. Surprisingly, this placement of adhesive could slightly change the operation of the eyelid cover. Since in FIG. 3A no adhesive is in the center of the backside 16 of the eyelid cover, the eyelid cover may fold away from the face outward (see FIG. 3B) instead of folding into the ocular cavity (see FIGS. 2A & 2C) when the eye is opened. The operation remains the same for FIGS. 3A and 3B as the preferred embodiment (FIGS. 1 & 2) when the eye is closed. However, the embodiment depicted in 3A and 3B would also necessitate an adhesive of stronger tackiness to remain on the eyelid, since less surface area of the back side 16 is devoted to adhesive.

Again, in FIG. 3C an alternate arrangement of adhesive dots 18 is provided where adhesive is placed on the back side 16, but only near the anterior edge 10. This placement of adhesive could slightly change the operation of the eyelid cover. Since in FIG. 3C no adhesive is in the center of the backside 16 of the eyelid cover nor is there any adhesive on the posterior edge 12 of the backside 16 of the eyelid cover, the eyelid cover will not fold into the ocular cavity (see FIG. 2); rather, the eyelid cover when the eye is opened will remain substantially flat but move atop the skin moving toward the eyebrow as depicted in FIG. 3D. The operation remains the same for FIGS. 3C and 3D as the preferred embodiment (FIGS. 1 & 2) when the eye is closed. However, the embodiment depicted in 3C and 3D would also necessitate an adhesive of stronger tackiness to remain on the eyelid, since less surface area of the back side 16 is devoted to adhesive.

FIGS. 4A and 4B depict an alternate embodiment that functions in the same operation as the preferred embodiment depicted in FIGS. 1 and 2. The use of layers of material in the composition of the eyelid cover can produce an eyelid cover that has increased light-blocking capabilities. The layers could be attached to each other by various means including adhesive, melting (if synthetic materials are used), weave or stitching, etceteras. These multitude of layers could be comprised of various materials including textiles, polymeric substances, etceteras.

FIG. 5 depicts an alternate embodiment where concentric lines 28 are drawn or printed on the top side 14 to indicate where a consumer should cut the device. These lines could be used to designate the place where the consumer should cut to tailor the device to their own eyelid shape and size. For example, three lines could be printed that relate to small, medium, or large sizes. The consumer could cut with scissors along these lines 28 to obtain a semi-individualized eyelid cover of better coverage and comfort than a one-size-fits-all eyelid cover.

Advantages

From the description above, a number of advantages of my eyelid covers become evident:

(a) Manufacturing of the invention is inexpensive since it is comprised of two parts in the preferred embodiment (i.e., adhesive and a silk fabric). Since eyelid covers are designed to fit on the eyelids, only a small amount of material is needed to manufacture each eyelid cover. Further, since the preferred embodiment is made of silk it is a naturally renewing and non-polluting resource from which to make the eyelid covers. Due to the low costs of manufacturing, a wide variety of consumers are able to purchase this product.

(b) The preferred embodiment use of silk fabric allows the invention to be light in weight.

(c) The preferred embodiment's use of silk fabric allows the invention to be bendable for storage or transport. Thus, it is easily portable to be used at home, while traveling, camping, in the field, or in any place where a portable light-blocking eyelid cover would be beneficial.

(d) The eyelid covers do not interfere with the sleep process. For example, the eyelid cover is comfortable, and does not create undue pressure on the face, eyes, or head even when contacting the pillow or another item that the individual is resting their head on while sleeping (e.g. a padded beam of an interior car door). Further, the present invention is barely detectable to the wearer and does not contribute to feelings of claustrophobia.

(e) The eyelid cover does not interfere with the physiological necessities of sleep. For example, the present invention can be put on before going to sleep and it does not need to be adjusted to obtain normal vision. Therefore, one can read before going to sleep with the eyelid covers on his/her eyelids, go to sleep without adjusting the eyelid covers, and open his/her eyes to see things with normal vision throughout the night and day. All of this can be accomplished without adjusting the eyelid covers and therefore without increasing physiological arousal which would interfere with sleep. Further, the invention is less likely to cause the claustrophobic reaction that sleep masks and prior art eyelid covers can evoke in some individuals. This elimination of the anxiety response of claustrophobia (due to the instant ability to see with the device on) contributes to the physiological necessities of sleep (i.e., people find that it is difficult to sleep while experiencing anxiety).

(f) The eyelid covers do not interfere with normal vision. The invention can be worn with the eyelids open or with the eyelids closed and the invention does not inhibit normal vision when the eyelids are open. The ability of the invention to accomplish this advantage is particularly useful for individuals that would like instant use of their sight. Some examples of these individuals could be vigilant sleepers that are concerned about visually checking the clock, checking unknown sounds in the room, or checking any potential safety threats while sleeping, such as possible house fires or intruders. Other individuals that could want instant use of their site include travelers in potentially unsafe settings or military soldiers in combat conditions that necessitate the instant assessment of threat and/or use of weaponry or machinery.

(g) The eyelid cover blocks a significant percentage of light from entering a closed eye by way of the eyelid. This is particularly useful while sleeping in environments that have less than optimal light conditions. The invention creates the effect of sleeping in a dark environment even if the environment actually contains light that would be bothersome to someone not using the invention.

(h) The eyelid cover is capable of being manufactured to block varying percentages of light from entering an eye by way of the eyelid. Various differences in manufacturing could produce eyelid covers of different abilities to block different amounts of light. This could be advantageous in that one individual may want an eyelid cover that blocks some, but not all light (50 percent for example). The individual may want this 50 percent blocking eyelid cover to effectively block diffuse sunlight coming through a curtain, but may still want to experience some light coming through the eyelid to aid in waking up. However, another individual may want an eyelid cover of a higher light-blocking percentage (for example 95 percent). A situation where this higher light-blocking eyelid cover may be useful is when trying to sleep in intense light environments, for example a soldier who must sleep in the desert sun or an individual that wants to block out as much ambient light as possible while sleeping late into the morning in their light-intense bedroom.

(i) The eyelid covers are a safe and comfortable sleep aid that blocks light from entering the eye by way of the eyelid, but does not interfere with normal vision. The preferred embodiment is made from a tightly woven natural black dyed silk fabric and non-allergenic adhesive. The product is conceptualized for the special use of sleeping, and addresses the various safety and comfort needs of a sleeper; namely, the need to have a device that 1 ) is not likely to abrade, lacerate, or irritate the eyeball, eyelid, face, or head; 2) effectively blocks light from entering a closed eye by way of the eyelid; 3) provides comfort in all sleeping conditions and does not exert unwanted pressure or sensations on the eyeball, eyelid, face, or head; and 4) enables the wearer to have full unencumbered use of his/her vision without adjusting the device, by simply opening his/her eyes.

CONCLUSION, RAMIFICATIONS, AND SCOPE

Accordingly, the reader will see that the eyelid covers of this invention can be used in any number of environments to help block unwanted light from entering the closed eye by way of the eyelid. In addition, the eyelid covers of this invention enable the wearer to have full unencumbered use of their vision by simply opening their eyes. There is no need to adjust or remove the eyelid covers to obtain normal vision. Further, the eyelid covers are safe and comfortable and are conceived to solve the numerous problems that are specific to the needs of a light-blocking device for use while resting, sleeping, or trying to fall asleep. The present invention has the additional advantages in that it provides an eyelid cover that is inexpensive to manufacture thereby increasing the likelihood that a wide variety of consumers will be able to purchase the invention;

provides an eyelid cover that is light in weight;

provides an eyelid cover that is easily portable to be used at home or while traveling, camping, or in any place where a portable light-blocking eyelid cover would be beneficial.

provides an eyelid cover that does not interfere with the sleep process. It provides for the necessities of sleep which include comfort and a lack of undesirable sensations.

provides an eyelid cover that does not interfere with the physiological necessities of sleep. For example, to provide an eyelid cover that one can put on before going to sleep and that does not need to be adjusted to obtain normal vision. Therefore, the wearer can get ready for bed or even read while wearing the device. Further, at night the wearer can instantly have use of his/her sight by simply opening his/her eyes. This reduces claustrophobia and reduces any anxiety. Dissimilar devices that interfere with vision (e.g., sleep masks) indirectly interfere with sleep by causing anxiety or claustrophobia for some individuals.

provides an eyelid cover that does not interfere with normal vision. The invention can be worn with the eyelids open or with the eyelids closed and the invention does not inhibit normal vision when the eyelids are open. The ability of the invention to accomplish this advantage is particularly useful for individuals that would like instant use of their sight. Some examples of these individuals could be vigilant sleepers that are concerned about visually checking the clock, checking unknown sounds in the room, or checking any potential safety threats while sleeping, such as possible house fires or intruders. Other individuals that could want instant use of their site include travelers in potentially unsafe settings or military soldiers in combat conditions that necessitate the instant assessment of threat and/or use of weaponry or machinery. Further, common everyday users will enjoy being able to put the device on while getting ready for bed, read in bed, then instantly go to sleep.

provides an eyelid cover that blocks a significant percentage of light from entering a closed eye by way of the eyelid.

provides an eyelid cover that is capable of being manufactured to block varying percentages of light from entering an eye by way of the eyelid. Various differences in manufacturing can produce eyelid covers of different abilities to block different amounts of light. For example, someone that wants to sleep in an intense light environment would need an eyelid cover of higher light-blocking ability than someone that simply wants to cut down on some ambient light, but still have the benefit of having some light enter the eye through the cover and eyelid to help wake him/her up.

provides a safe and comfortable sleep aid that blocks light from entering the eye by way of the eyelid but does not interfere with normal vision. Because the preferred embodiment is made of silk and hypoallergenic adhesive, it is extremely safe and highly unlikely to scratch the eyeball even if it comes into direct contact with the eyeball while sleeping or while applying or removing the invention. Safety, comfort, and an ability to quickly use one's sight are important issues that are needed for restful sleep and these qualities are assured by the conceptualization of the invention.

While the above description contains numerous specificities, these should not be construed as limiting the scope of the invention, but as merely providing illustrations of some of the presently preferred embodiments of this invention. Many other ramifications and variations are possible within the teachings of the invention. For example the eyelid cover could be composed of any number of materials such as synthetic material; the eyelid covers could be made of a composition of materials such as a laminate of different layers of synthetic fabric such as nylon and natural fabric such as cotton or silk; the eyelid covers could have a bridge of some kind connecting the two covers together to form one unit, etceteras.

Thus, the scope of the invention should be determined by the appended claims and their legal equivalents, and not by the examples given.

| Definition List 1 | |
|---|---|
| Term | Definition |
| Adhesive | Any substance used to bond two or more surfaces together |

| Definition List 2 | |
|---|---|
| Term | Definition |
| Sheet member | Any material that is uniform, thin, and flat |

| Definition List 3 | |
|---|---|
| Term | Definition |
| polymeric | Made of polymers (i.e., plastics) |

What is claimed is:

1. A new method for improving the quality and quantity of human sleep by blocking a substantial amount of light from entering a closed eyelid while permitting normal sight when the eyelid is opened by way of an eyelid cover where adhesive is placed on the back side along the anterior and posterior edges of the eyelid cover dictating the mechanism of action to fold the eyelid cover away from the ocular cavity when the user opens his/her eye, enabling uninhibited use of vision, comprising:
   a. providing an eyelid cover of the type comprising a thin sheet member of flexible, substantially light-blocking, materials,
   b. providing an adhesive on the back side of the eyelid cover along the anterior and posterior edges for affixing said thin sheet member of flexible, substantially light-blocking, materials to the outer skin of the eyelid,
   c. affixing said eyelid cover to the outer skin of a human eyelid,
   d. blocking of substantial amounts of light from entering the eye by way of said eyelid,
   e. permitting normal sight when said eyelid is opened, by the movement of the upper eyelid moving said eyelid cover away from the field of view due to a mechanism of action that results in folding the eyelid cover away from the ocular cavity without removing said eyelid cover,
whereby said eyelid cover provides the user with a safe, comfortable, and easy way to enhance his/her ability to sleep in environments where there is unwanted light while maintaining the ability to have uninhibited use of vision by opening his/her eyes.

2. The method of claim 1 wherein said sheet member of flexible, substantially light-blocking, material is comprised of textiles.

3. The method of claim 1 wherein said sheet member of flexible, substantially light-blocking, material is comprised of silk.

4. The method of claim 1 wherein said sheet member of flexible substantially light-blocking, material is comprised of polymeric materials.

5. The method of claim 1 wherein said sheet member of flexible, substantially light-blocking, material is comprised of a multitude of layers of materials.

6. A new method for improving the quality and quantity of human sleep by blocking a substantial amount of light from entering a closed eyelid while permitting normal sight when the eyelid is opened by way of an eyelid cover where adhesive is placed on the back side along the anterior edge of the eyelid cover dictating the mechanism of action to slide the eyelid cover away from the field of view moving it towards the eyebrow when the user opens his/her eye, enabling uninhibited use of vision comprising:
   a. providing an eyelid cover of the type comprising a thin sheet member of flexible, substantially light-blocking, materials,
   b. providing an adhesive on the back side of the eyelid cover along the anterior edge for affixing said thin sheet member of flexible, substantially light-blocking, materials to the outer skin of the eyelid,
   c. affixing said eyelid cover to the outer skin of a human eyelid,
   d. blocking of substantial amounts of light from entering the eye by way of said eyelid,
   e. permitting normal sight when said eyelid is opened, by the movement of the upper eyelid moving said eyelid cover away from the field of view due to a mechanism of action that results in sliding the eyelid cover away from the field of view towards the eyebrow without removing said eyelid cover, whereby said eyelid cover provides the user with a safe, comfortable, and easy way to enhance his/her ability to sleep in environments where there is unwanted light while maintaining the ability to have uninhibited use of vision by opening his/her eyes.

7. The method of claim 6 wherein said sheet member of flexible, substantially light-blocking, material is comprised of textiles.

8. The method of claim 6 wherein said sheet member of flexible, substantially light-blocking, material is comprised of silk.

9. The method of claim 6 wherein said sheet member of flexible, substantially light-blocking, material is comprised of polymeric materials.

10. The method of claim 6 wherein said sheet member of flexible, substantially light-blocking, material is comprised of a multitude of layers of materials.

* * * * *